(12) United States Patent
Gonzalez

(10) Patent No.: US 10,294,156 B2
(45) Date of Patent: May 21, 2019

(54) COMPOSITES HAVING NOVEL ORGANIC COMPONENTS AND METHODS OF MANUFATURE

(71) Applicant: Marcos Gonzalez, Davie, FL (US)

(72) Inventor: Marcos Gonzalez, Davie, FL (US)

(*) Notice: Subject to any disclaimer, the term of this patent is extended or adjusted under 35 U.S.C. 154(b) by 251 days.

(21) Appl. No.: 14/428,369

(22) PCT Filed: Mar. 28, 2013

(86) PCT No.: PCT/US2013/034404
§ 371 (c)(1),
(2) Date: Mar. 15, 2015

(87) PCT Pub. No.: WO2014/042696
PCT Pub. Date: Mar. 20, 2014

(65) Prior Publication Data
US 2018/0111877 A1   Apr. 26, 2018

(51) Int. Cl.
C12P 19/00 (2006.01)
C04B 24/00 (2006.01)
C12N 1/12 (2006.01)
C12P 1/00 (2006.01)
C04B 26/00 (2006.01)
C04B 28/02 (2006.01)
C04B 20/10 (2006.01)
C04B 22/06 (2006.01)
C04B 26/28 (2006.01)
C12N 1/20 (2006.01)
C04B 103/10 (2006.01)
C04B 103/30 (2006.01)

(52) U.S. Cl.
CPC .......... C04B 24/00 (2013.01); C04B 20/1022 (2013.01); C04B 22/066 (2013.01); C04B 26/00 (2013.01); C04B 26/006 (2013.01); C04B 26/285 (2013.01); C04B 28/021 (2013.01); C12N 1/12 (2013.01); C12N 1/20 (2013.01); C12P 1/00 (2013.01); C04B 2103/10 (2013.01); C04B 2103/30 (2013.01); Y02W 30/92 (2015.05); Y02W 30/97 (2015.05)

(58) Field of Classification Search
CPC ....................................... C12P 19/00
See application file for complete search history.

(56) References Cited

U.S. PATENT DOCUMENTS

2011/0086386 A1* 4/2011 Czartoski ................. C12N 1/06
435/67

* cited by examiner

Primary Examiner — Rosanne Kosson
(74) Attorney, Agent, or Firm — B. Y. Mathis

(57) ABSTRACT

Various methods for making material capable of forming structural composites are disclosed. For example, a particular method may include growing an amount of cyanotic organisms, separating cell walls of the cyanotic organisms from internal portions of the cyanotic organisms to form a purified algae extract, the purified algae extract being from the internal portions of the cyanotic organisms, and applying an effective amount of alkaline water to the purified algae extract to form a balanced algae extract having little or no chemical reactivity, wherein a pH of the alkaline water is a function of a pH of the purified algae extract.

16 Claims, 4 Drawing Sheets

COMPOSITES HAVING NOVEL ORGANIC COMPONENTS AND METHODS OF MANUFATURE

This application is a continuation/draws priority from, and incorporates the entire content of, PCT Application No. PCT/US13/34404 entitled "COMPOSITES HAVING NOVEL ORGANIC COMPONENTS AND METHODS OF MANUFATURE" filed on Mar. 28, 2013, by inventor Marcos Gonzalez.

BACKGROUND

I. Field

This disclosure relates to elasto-polymers or other concrete-like materials using algae-produced materials for plasticizers, accelerants and/or bonding agents.

II. Background

The term "geopolymer" refers to a class of synthetic aluminosilicate materials with potential use in a number of areas, but predominantly as a replacement for Portland cement. Compared to Portland cement, however, geopolymers are unduely expensive and have therefore been a failure commercially. Further, geopolymer chemistry is dependent on petrochemicals.

SUMMARY OF THE INVENTION

Various methods for making material capable of forming structural composites are disclosed. For example, a particular method may include growing an amount of cyanotic organisms, separating cell walls of the cyanotic organisms from internal portions of the cyanotic organisms to form a purified algae extract, the purified algae extract being from the internal portions of the cyanotic organisms, and applying an effective amount of alkaline water to the purified algae extract to form a balanced algae extract having little or no chemical reactivity, wherein a pH of the alkaline water is a function of a pH of the purified algae extract. The pH-balanced algal extract is coated on particles to form a plasticizer or added to an aggregate mixture to make both a plasticizer and a bonding agent.

BRIEF DESCRIPTION OF THE DRAWINGS

The features and nature of the present disclosure will become more apparent from the detailed description set forth below when taken in conjunction with the accompanying drawings in which reference characters identify corresponding items.

FIG. 3B depicts a substrate particle covered with a balanced algae extract coating.

DETAILED DESCRIPTION

Figure 1:
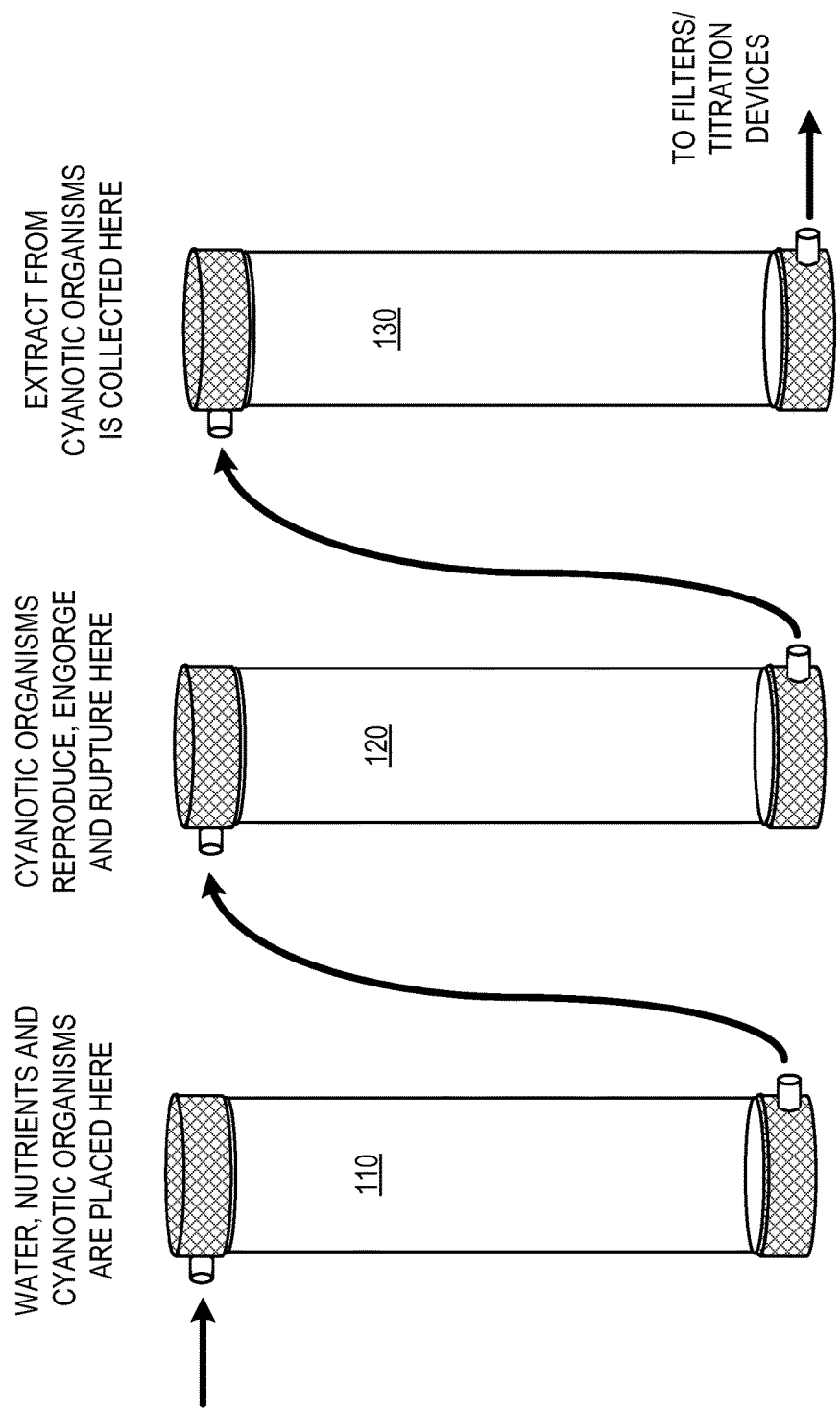
FIG. 1 is an example bioreactor usable to grow green and/or cyanotic organisms and harvest organic extracts.

The disclosed methods and systems below may be described generally, as well as in terms of specific examples and/or specific embodiments. For instances where references are made to detailed examples and/or embodiments, it should be appreciated that any of the underlying principals described are not to be limited to a single embodiment, but may be expanded for use with any of the other methods and systems described herein as will be understood by one of ordinary skill in the art unless otherwise stated specifically.

The following definitions apply for this disclosure:

The term "aggregate" refers to a component of a composite material used to resist compressive or tensile stresses.

The term "structural composite" refers to a concrete, a geopolymer, an elasto-polymer or a cryptobiotic material.

The term "polymer" refers to a class of materials composed of repeating structural units. These structural units are typically connected by covalent chemical bonds. Although the term "polymer" is sometimes taken to refer only to plastics, the term encompasses a large class of compounds with a wide variety of properties.

The term "biomineralization" refers to a process by which certain living organisms take various compounds from their environment to produce specialized minerals—often to harden or stiffen various tissues. Past man-made attempts to produce similar minerals that various organisms produce easily have largely been a failure as they are energy inefficient, and require stringent conditions, such as high temperature, pressure or extreme pH levels.

The class of materials disclosed below are referred to as "Elasto-Polymers," ("EPs") or "Geo-Elasto-polymers," ("GEPs") and are meant to refer to a class of materials that can take anything from a slightly elastic to rock-like form, and which is based in part on what is believed to be a synthetic biomineralization using organic molecules and/or induced covalent bonding cased by organic substances.

The organic components in the materials described below are taken from any of a variety of green or blue-green alga species, such as *Synechocystis*. It is to be appreciated that the terms "cyanobacteria" and "blue-green algae" are often, but not always, used synonymously in science and industry. The American Heritage dictionary defines cyanobacteria as follows: "Cyanobacteria Cy•a•no•bac•te•ri•a (sī' ə -nō-bāk-tēr' ē- ə ) n. A group of Procaryotae consisting of unicellular or filamentous gram-negative microorganisms that are either nonmotile or possess a gliding motility, may reproduce by binary fission, and photosynthetically produce oxygen; some species capable of fixing nitrogen. Members of this phylum were formerly called blue-green algae." *The American Heritage® Stedman's Medical Dictionary* (2002)

However, there may be modern distinctions between cyanobacteria and eukaryotic organisms (algae) based on anatomical differences not relevant to this disclosure. It is to be appreciated in light of the following disclosure that the two terms are meant to be equivalents given their traditional, rather than recently emerged, definitions, unless otherwise stated or claimed.

However, for the purposes of distinguishing the two types of organisms, when necessary, to differentiate different attributes of the two classes of organisms (cyanobacteria and eukaryotic organisms), and for the sake of claiming, the terms will be considered as different organisms while the generic term "cyanotic organism" shall be used to refer to both organisms, as well as later equivalent organisms that may later be discovered, synthetically developed (e.g., genetically engineered or selectively bred), or later recognized.

Another distinction to be made is that of single-cell algae and seaweed. "Seaweed" is a loose colloquial term encompassing macroscopic, multicellular, benthic marine algae. The term includes some members of the red, brown and green algae. For the purpose of this document, cyanotic organisms are considered to be distinct from seaweed.

A particular ingredient useful in the production of concrete and elastopolymers is known as a "plasticizer." Plasticizers are water reducers or dispersants that can be added to concrete or other composite mixtures to improve workability. Generally, the strength of a concrete is inversely proportional to the amount of water added or water-cement (w/c) ratio. In order to produce a stronger concrete/composite, less water is added. Too little water, however, "starves" the mix, which makes the concrete/composite mixture very unworkable and difficult to mix, necessitating the use of plasticizers.

This disclosure describes a novel process and mixtures capable of producing structural composites suitable as a building material. The process and resultant materials can produce structures that are both low-cost and durable compared to structures made of conventional building materials, such as Portland cement or geopolymers.

FIG. 1 is an example bioreactor 100 usable to grow green algae and/or cyanotic organisms and harvest organic extracts. The example bioreactor 100 includes three tanks including a first tank 110, a second tank 120 and a third tank 130. Usage of the tanks 110, 120 and 130 will be discussed below with reference to FIG. 4 (steps S400-S406), which outlines a method for growing green and/or cyanotic organisms, and harvesting a resultant algae extract.

Figure 4:
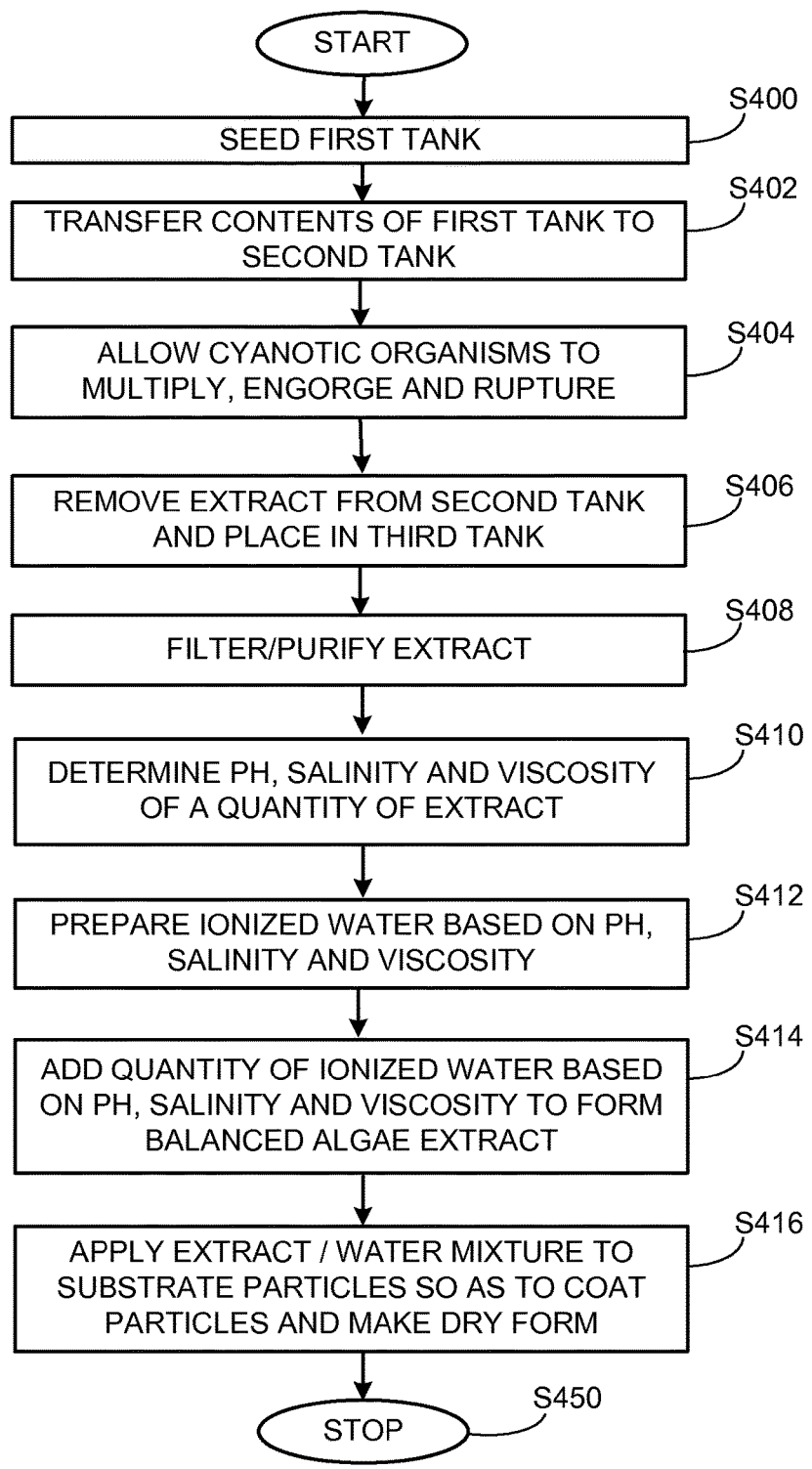
FIG. 4 is a flowchart outlining an exemplary operation for growing cyanotic organisms and harvesting organic extracts.

The process of FIG. 4 starts in step S400 where one or more targeted species of green or cyanotic organisms is cultured. In the non-limiting example of this disclosure, the cyanotic organisms used may include *Synechocystis* (PCC 6803) and/or any number of species of the collenia genus noting that there may be a wide range of suitable microbes, including microbes more recently distinguished as algae. Because these organisms can reproduce asexually, they can be cultured in bioreactors by a photosynthesis process. In the present example, the first tank 110 is used to culture the selected cyanotic organisms by placing them in a solution of water and nutrients, such as any number of proteins (e.g., laminin, myosin, collagen, actin and/or keratin), selenium, triphosphates, magnesium sterate, salt, magnesium oxide, methosol, barium, carbon dioxide, and so on. The particular mixture of nutrients can vary according to a large range of criteria, such as the type of organism(s) used and varying environmental conditions.

At step S402, the medium and cyanotic organisms are transferred from the first tank to a second tank (such as tank 120 of FIG. 1) where in step S404 the cyanotic organisms are allowed to multiply, engorge and rupture as a result of over-engorgement within limited space. It is to be appreciated, however, that the cell walls of the organisms may be broken by any number of known or later-developed processes, such as mechanically slicing cell walls or rupturing cell walls by some other mechanism, such as a high-speed blending process, application of ultra-sonic energy, chemical treatment, and so on.

Next, in step S406, the algae extract, which contains various yet-unidentified and identified enzymes and proteins, are removed from the second tank and transferred to a third tank (e.g., tank 130 of FIG. 1), where the algae extract is stored.

Figure 2:
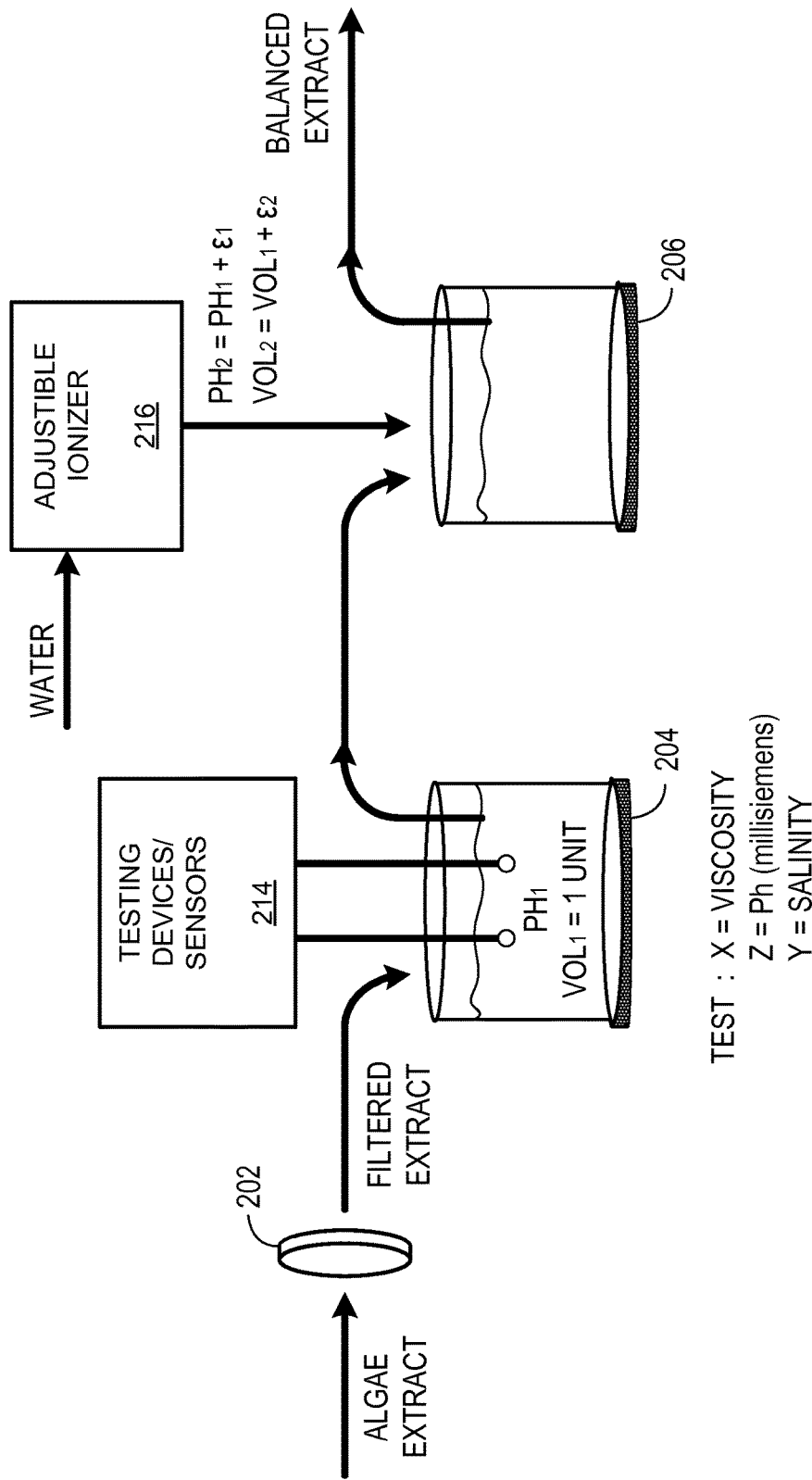
FIG. 2 depicts example equipment used to process the organic extracts of FIG. 1.
Figure 3:
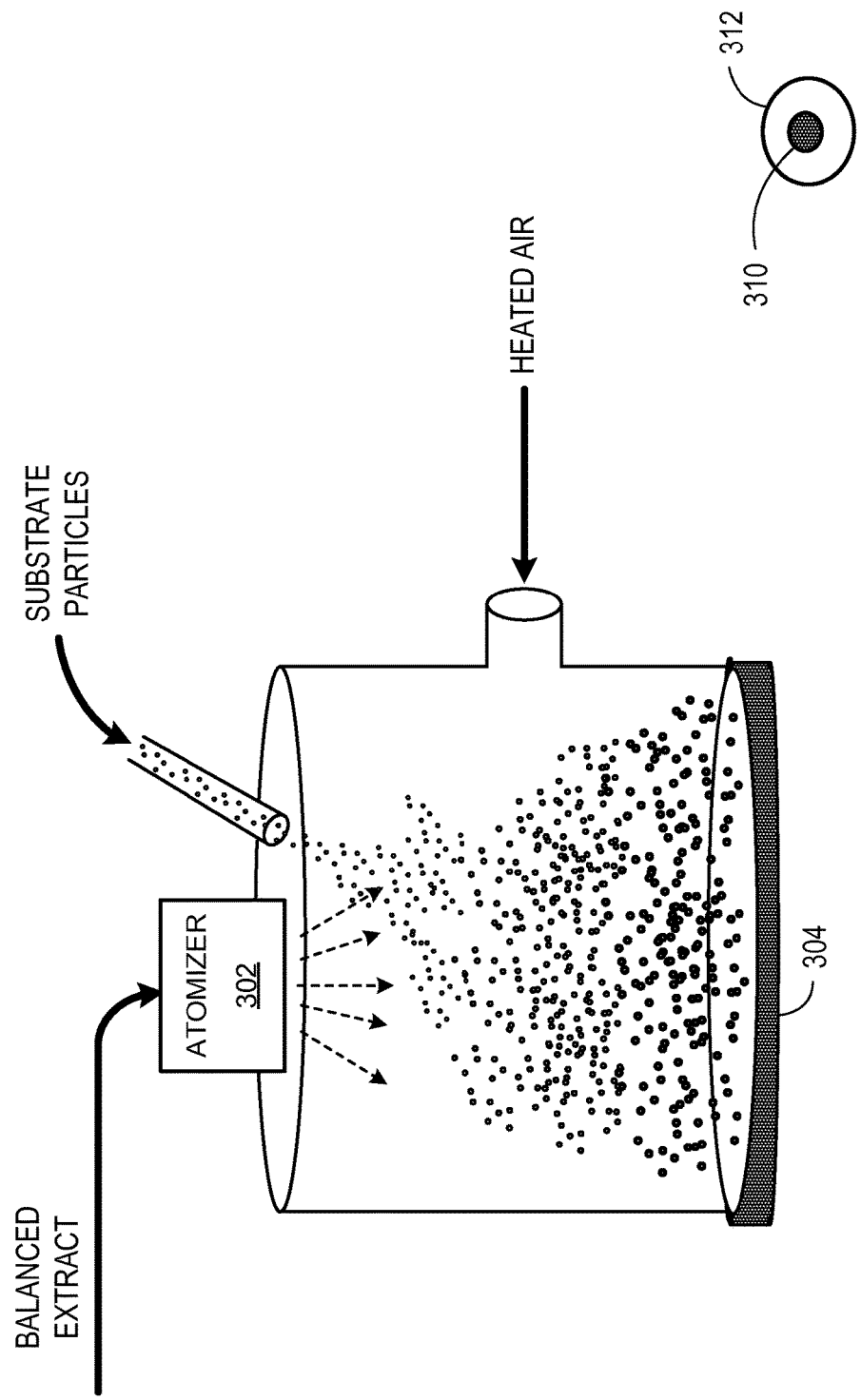
FIG. 3 depicts example equipment used to further process the organic extracts of FIGS. 1-2 so as to create a dry-storage form of the organic extract.

FIGS. 2-3 depict example equipment used to process the organic extracts of FIG. 1 and steps S400-S406. Such example equipment includes a filter 202, a first storage unit 204, testing equipment 214, a second storage unit 206, an adjustable ionizer 216, coating chamber 304 and atomizer 302. Usage of devices 202-304 will be discussed below with reference to FIG. 4 (steps S408-S450), which outlines a method for processing the algae extract of steps S400-S406.

In step S408, the algae extract is further processed/purified by various filtering procedures intended to remove algae cell walls and other contaminants. Such filtering can be performed with, for example, the filter 202 of FIG. 2. Filter 202 may take the form of a membrane filter, other forms of filters, a centrifuge or any other known or later-developed device capable of separating the interior of algae cells from respective cell walls and other contaminants. For the purpose of this disclosure, the filtered portion of the extract may be referred to as a "filtered extract" or "purified extract." It is to be appreciated that the purified extract may now be optionally combined with any number of proteins, e.g., laminin, myosin, collagen, actin and/or keratin.

Next, in step S410, the filtered/purified extract, which can take the form of a generally clear viscous syrup, is tested to determine viscosity, pH and salinity, which can vary from batch to batch as a function of different algae types, different nutrients added and different environmental conditions. Testing can be performed by the testing devices/sensors 214 of FIG. 2, which can include, for example, a viscometer or rheometer, a digital pH meter or pH test strips, and any number of commercially available salinity testing devices.

Next, in step S412, a quantity of ionized water is prepared based on the viscosity, pH and/or salinity. Such ionized water can be produced using, for example, the adjustable ionizer 216 of FIG. 2. It is expected that the pH of the purified extract (defined as $pH_1$) will be positive/alkaline. Accordingly, the pH of water produced by the adjustable ionizer 216 (defined as $pH_2$) will also be alkaline and carry a substantial number of hydroxide (OH—) ions. Generally, $pH_2 = pH_1 + \varepsilon_1$, with $\varepsilon_1$ being defined as a first error-adjustment factor that will vary as a function of the salinity and viscosity. Generally, $\varepsilon_1$ will increase with viscosity and increase with salinity, but the exact amount of adjustment/error may vary according to the algae type(s) and nutrients used. For the purpose of claim construction, the term "generally equal" as it pertains to relative volumes refers to an expected range about a median value that can be determined by one of ordinary skill in the art using a particular set of conditions. As variables, such as viscosity, can easily change depending on, for example, equipment used, environmental conditions (and ranges thereof), nutrient mix and cyanotic organism, the range of "generally equal" should be determined using an experimental baseline according to detailed algae production controls.

As with the pH, the quantity/volume of added ionized water can vary. Generally, the amount of added ionized water $(VOL_2)$=the volume of purified extract $(VOL_1)+\varepsilon_2$, with $\varepsilon_2$ being defined as a second error-adjustment factor that will vary as a function of the salinity and viscosity. Generally, $\varepsilon_2$ will increase with viscosity and increase with salinity, but the exact amount of adjustment/error again may vary according to the algae type(s) and nutrients used.

Then, in step S414, the quantity/volume $(VOL_2)$ of ionized water is added to the quantity/volume $(VOL_1)$ of purified extract. In this step, the ionized water, when properly prepared and mixed to the purified algae extract, causes the purified extract to be "structurally balanced" so as to stop the purified extract from reacting with its environment and become chemically static. That is, enzyme molecules normally in a transient/changing state are stabilized by the hydroxide ions by causing the enzyme molecules to become polarized so as to structurally repel other molecules in suspension. Thus, the algae extract has little reactivity or no chemical reactivity with the term "little reactivity" meaning that there is a low enough level of chemical degradation such that the balanced algae extract would be still commercially viable after at least several weeks of storage.

In step S416, the balanced extract can be applied to a carrier to make a "Dry Form Plasticizer" ("DFP"), which has a commercial advantage of being in an industry familiar form capable of being easily stored, re-hydrated and/or mixed with aggregates.

FIG. 3 depicts an example apparatus where substrate particles, such as round, smooth particles of silicon 310 (or another mineral) are covered with a balanced extract coating 312. See, FIG. 3B. In operation, the balanced algae extract is passed through an atomizer 302 into tank 304. Substrate particles, such as round, smooth particles of silicon 310, are subjected to the balanced extract. By virtue of hot air injected into tank 304, a coating of increasing size will accumulate around the individual particles until the coated particles become large and heavy enough to fall to the bottom of tank 304, where they can layer be removed.

The nature of the DFP is two-fold. First, it provides an excellent non-toxic and natural plasticizer when making composite materials, such as concrete. Second, when made from a properly balanced algae extract, the DFP has an unexpected property of forcing covalent bonds among a large variety of substances, and can compel what appears to be a form of biomineralization of organic materials, such as sawdust and seed husks.

The balanced dry-form extract/plasticizer, when used as a plasticizer for a composite material, initially compels a hydrophilic reaction by absorbing water. Subsequently, the same extract causes a hydrophobic reaction of the composite material by expelling water as covalent bonds are formed by the resultant composite material. The second process occurs when added water disrupts the previously attained pH balance in step S414.

The steps above can produce polycarboxylate ethers (PCE) or just polycarboxylate (PC). PCE/PC represents a new generation of plasticizers that are not only chemically different from the older sulfonated melamine and naphthalene-based products, but their action mechanism is also different. That is, PCE/PC can act by causing particle dispersion of a composite by steric stabilisation. In contrast, conventional plasticizers use an electrostatic repulsion effect to achieve particle dispersion.

The steric stabilisation form of dispersion is more powerful in its effect and gives improved workability retention to the cementitious mix. Furthermore, the chemical structure of PCE allows for a greater degree of chemical modification than the older-generation products, offering a range of performance that can be tailored to meet specific needs.

Industrial Applications

The extract (or any number of modified or purified extracts) may be added to an aggregate mixture for concrete or any number of concrete or elastopolymer formulations. With regard to elastopolymers, a theory arises that sepiolite (e.g., polygorskite with a biofilm blend of enzymes and genus species of cryptomatic soils and cyanobacteria cultures) can act as carrier minerals that break down as the alkalinity rises, thus delivering soluble and mobile $SiO_2$ and $Al_2O_3$ for pozzolanic reactions that form more polymeric minerals. In various embodiments, the reaction may be accelerated with reactive magnesium oxide, which can produce stronger bonds and control the PH during the reaction curve. Polycondensation of organic substances (natural polymers, proteins, enzymes and minerals produced organic and inorganically by chemical reactions that result in cross-linked through hydrogen bonding forming covalent bonds of aggregates and materials, which in turn may form cryptomatic composites.

The combination of the biofilm (enzymes) produced by the algae microbes with keratin and laminin can produce an effective bonding agent by geosynthesis to, in turn, create covalent bonds with a cross-linking matrix in combination with conventional aggregates when combined with aluminum silacate, selenium, humic acid, sodium metasilrate reactive magnesium oxide and fly ash.

EXAMPLES

Example 1: a combination of 10% DFP (by weight) can be added to 30% pozzolanic materials, 30% AlSi (fly ash) and 30% limestone power can be mixed, with some other aggregate(s), e.g., sand or stones, to create a concrete-like material with compression and tensile strength superior to Portland cement. The resultant material may be made with a near-zero co-efficient of expansion, impervious to water, highly resistant to corrosives, such as acid. For example, a cube of the resultant composite was subjected to a 30% HCL bath for 160 hours, but lost only 0.2% mass. In contrast, a similar-sized cube of Portland was dissolved to a mushy consistency. The resultant composite is estimated to be 20%-30% cheaper to manufacture than Portland, and has a negative carbon footprint.

Example 2: a wood substitute may be made using a combination of 10% DFP (by weight), 20% pozzolanic materials, 50% fly ash and 20% silica. Aggregates, such as sawdust, seed husks or some other cellulose-bearing material, may be added. The resultant material may be worked much as wood can be worked, but will not burn even with the application of an oxy-acetylene torch. The resultant material has a mechanical flexibility similar to wood, but is not subject to rot.

Example 3: a combination of 20% DFP (by weight) can be added to 50% AlSi, and 30% metallic grindings/powders, such as zinc, iron and copper. The resultant material may be made with a near-zero co-efficient of expansion, impervious to water, highly resistant to corrosives, such as acid.

Example 4: an extract may be applied to parallel strands of hollow and porous basalt fibers, then allowed to cure to a rebar-like form. The rebar-equivalent is about $\frac{1}{6}^{th}$ the weight, cheaper to manufacture, impervious to corrosion and has a far superior tensile strength.

Example 4: an extract may be applied to a flat weave of hollow and porous basalt fibers, then allowed to cure. The resultant product resembles fiberglass composites, but with better strength and insulative properties.

Example 5: a composite similar to that of example 1 may be made with increased amounts of DFP. The resultant product resembles concrete, but has a capacity to better absorb vibrations, which can be valuable to produce foundations for generators or motors as it will extend the service life of internal moving parts, such as bearings.

The percentage of extract may vary, but it is envisioned that an effective amount of extract may, depending on variations of aggregates and chemistry, range from about 0.5% to 5%, e.g., 1%-3%. Adding greater amounts of the extract can cause the resultant material to take on more plastic-like qualities.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of forming an algae-based extract, comprising:
    (a) growing an amount of cyanotic organisms;
    (b) separating cell walls of the cyanotic organisms from internal portions of the cyanotic organisms to form a purified algae extract, the purified algae extract being from the internal portions of the cyanotic organisms; and
    (c) adding an effective amount of alkaline water to the purified algae extract to form a balanced algae extract having little or no chemical reactivity, wherein the pH of the alkaline water is a function of the pH of the purified algae extract; and
    (d) coating substrate particles with the balanced algae extract to form a dry-form plasticizer.

2. The method of claim 1, wherein the pH of the alkaline water is a function of at least two of the pH of the purified algae extract, the viscosity of the purified algae extract and the salinity of the purified algae extract.

3. The method of claim 2, wherein the pH of the alkaline water is a function of the pH of the purified algae extract, the viscosity of the purified algae extract and the salinity of the purified algae extract.

4. The method of claim 1, wherein the volume of the alkaline water added to the purified algae extract is substantially equal to the volume of the purified algae extract.

5. The method of claim 1, wherein the volume of the alkaline water added to the purified algae extract is a function of the volume of the purified algae extract and the viscosity of the purified algae extract.

6. The method of claim 5, wherein the volume of the alkaline water added to the purified algae extract is also a function of the salinity of the purified algae extract.

7. The method of claim 1, wherein growing the cyanotic organisms includes feeding the cyanotic organisms laminin and keratin.

8. The method of claim 1, wherein the cyanotic organisms include one or more cyanobacteria.

9. The method of claim 8, at least one cyanobacterium is of the genus *Synechocystis*.

10. The method of claim 1, wherein the cyanotic organisms include a eukaryotic organism.

11. A method of forming an algae-based extract, comprising:
    (a) growing an amount of cyanotic organisms, wherein the cyanotic organisms include a cyanobacterium;
    (b) separating cell walls of the cyanotic organisms from internal portions of the cyanotic organisms to form a purified algae extract, the purified algae extract being from the internal portions of the cyanotic organisms;
    (c) adding an effective amount of alkaline water to the purified algae extract to form a balanced algae extract having little or no chemical reactivity, wherein the pH of the alkaline water is a function of the pH of the purified algae extract, the viscosity of the purified algae extract and the salinity of the purified algae extract, and wherein the volume of the alkaline water added to the purified algae extract is a function of the volume of the purified algae extract and the viscosity of the purified algae extract; and
    (d) coating substrate particles with the balanced algae extract to form a dry-form plasticizer.

12. A method of forming a hard composite, comprising:
    (a) growing an amount of cyanotic organisms that include at least cyanobacteria;
    (b) separating cell walls of the cyanotic organisms from internal portions of the cyanotic organisms to form a purified algae extract, the purified algae extract being from the internal portions of the cyanotic organisms;
    (c) adding an effective amount of alkaline water to the purified algae extract to form a balanced algae extract having little or no chemical reactivity, wherein the pH of the alkaline water is a function of the pH of the purified algae extract; and
    (d) adding an effective amount of the balanced algae extract to an aggregate mixture so as to provide both a plasticizer and a bonding agent that causes covalent bonds to form in the aggregate mixture.

13. The method of claim 12, wherein the aggregate mixture further includes an effective amount of reactive magnesium oxide acting as an accelerant.

14. The method of claim 12, wherein the balanced algae extract is added in the ratio of 1%-3% by weight to the aggregate mixture.

15. The composite of claim 12, wherein the aggregate mixture further includes aluminum silacate, selenium, humic acid, sodium metasilrate, reactive magnesium oxide and fly ash.

16. The composite of claim 12, wherein the aggregate mixture further includes sawdust and/or seed husks.

* * * * *